United States Patent [19]

Böger et al.

[11] Patent Number: 4,812,466
[45] Date of Patent: Mar. 14, 1989

[54] PYRIDYLOXY-SUBSTITUTED PHENYLCARBODIIMIDES AS PESTICIDES

[75] Inventors: Manfred Böger, Weil am Rhein, Fed. Rep. of Germany; Jozef Drabek, Oberwil, Switzerland

[73] Assignee: Ciba-Geigy Corporation, Ardsley, N.Y.

[21] Appl. No.: 115,633

[22] Filed: Oct. 26, 1987

Related U.S. Application Data

[63] Continuation of Ser. No. 776,257, Sep. 16, 1985, abandoned.

[30] Foreign Application Priority Data

Sep. 19, 1984 [CH] Switzerland .................. 4479/84
Aug. 15, 1985 [CH] Switzerland .................. 3526/85

[51] Int. Cl.$^4$ .................. C07D 213/64; A01N 43/40
[52] U.S. Cl. .................. 514/351; 546/300; 564/252
[58] Field of Search .................. 546/300; 514/351; 564/252

[56] References Cited

U.S. PATENT DOCUMENTS 4,101,675  7/1978  Panneman .................. 514/632
4,537,620  8/1985  Pallos .................. 71/94
4,559,353  12/1985  Turnbull .................. 514/346

FOREIGN PATENT DOCUMENTS 2553259  6/1977  Fed. Rep. of Germany ...... 564/252
1064257  4/1967  United Kingdom .................. 562/252

OTHER PUBLICATIONS

Liebigs Ann. Chem. 718, pp. 24–32 (1968).
Liebigs Ann. Chem. (1) 1984.
J. Chem. Soc. pp. 2640–2646 (1968).
Bull. Chem. Soc. Japan, 53 No. 9, pp. 2582–2585 (1980).
Indian Journal of Chem., vol. 19B (8/80) pp. 672–675.
Synthesis, International Journal of Methods in Synthetic Organic Chemistry 1577, No. 12, Dec., R. Rossi.

*Primary Examiner*—Alan L. Rotman
*Attorney, Agent, or Firm*—Kevin T. Mansfield; Edward McC. Roberts

[57] ABSTRACT

The invention relates to novel substituted carbodiimides of the formula

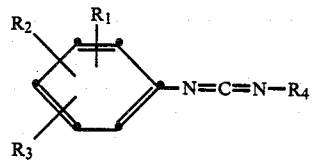

wherein
$R_1$ is hydrogen, halogen, $C_1$–$C_{10}$alkyl, $C_1$–$C_5$alkoxy, $C_1$–$C_5$alkoxy which is substituted by 1 to 7 halogen atoms, or is $C_1$–$C_5$alkylthio;
$R_2$ is hydrogen, halogen, $C_1$–$C_{10}$alkyl or $C_1$–$C_5$alkoxy;
$R_3$ is hydrogen, $C_1$–$C_{10}$alkyl, halogen, phenoxy, phenylthio, or is phenoxy or phenylthio, each mono- or disubstituted by a member selected from the group consisting of halogen, methyl, ethyl, $C_1$–$C_3$haloalkyl containing 1 to 7 halogen atoms and cyano, or is pyridyloxy or pyridyloxy which is mono- or disubstituted by a member selected from the group consisting of halogen and $C_1$–$C_3$haloalkyl containing 1 to 7 halogen atoms;
$R_4$ is $C_1$–$C_{12}$alkyl, alkoxyalkyl containing a total of 2 to 10 carbon atoms, $C_3$–$C_{10}$cycloalkyl, $C_3$–$C_{10}$cycloalkylmethyl, $C_3$–$C_{10}$cycloalkyl which is substituted by 1 to 3 $C_1$–$C_3$alkyl groups, or is $C_1$–$C_5$alkyl which is substituted to 1 or 2 $C_3$–$C_{10}$cycloalkyl groups, or is a polycyclic alkyl group containing 7 to 10 carbon atoms, phenyl($C_1$–$C_5$)alkyl or phenyl($C_1$–$C_5$)alkyl which is mono- or disubstituted at the phenyl nucleus by halogen, trifluoromethyl, methoxy or ethoxy, to the preparation of these compounds and to compositions containing them for use in pest control, especially for controlling insects and representatives of the order Acarina that attack plants and animals, in particular plant-destructive sucking insects.

19 Claims, No Drawings

PYRIDYLOXY-SUBSTITUTED PHENYLCARBODIIMIDES AS PESTICIDES

This application is a continuation of application Ser. No. 776,257, filed 9/16/85, abandoned.

The present invention relates to novel substituted N-phenyl-N'-alkylcarbodiimides, to the preparation thereof and to the use thereof in pest control.

The compounds of the invention are of formula I

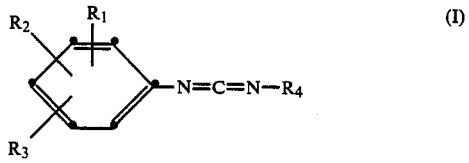

wherein $R_1$ is hydrogen, halogen, $C_1$-$C_{10}$alkyl, $C_1$-$C_5$alkoxy, $C_1$-$C_5$alkoxy which is substituted by 1 to 7 halogen atoms, or is $C_1$-$C_5$alkylthio;

$R_2$ is hydrogen, halogen, $C_1$-$C_{10}$alkyl or $C_1$-$C_5$alkoxy;

$R_3$ is hydrogen, $C_1$-$C_{10}$alkyl, halogen, phenoxy, phenylthio, or is phenoxy or phenylthio, each mono- or disubstituted by a member selected from the group consisting of halogen, methyl, ethyl, $C_1$-$C_3$haloalkyl containing 1 to 7 halogen atoms and cyano, or is pyridyloxy or pyridyloxy which is mono- or disubstituted by a member selected from the group consisting of halogen and $C_1$-$C_3$haloalkyl containing 1 to 7 halogen atoms;

$R_4$ is $C_1$-$C_{12}$alkyl, alkoxyalkyl containing a total of 2 to 10 carbon atoms, $C_3$-$C_{10}$cycloalkyl, $C_3$-$C_{10}$cycloalkylmethyl, $C_3$-$C_{10}$cycloalkyl which is substituted by 1 to 3 $C_1$-$C_3$alkyl groups, or is $C_1$-$C_5$-alkyl which is substituted by 1 or 2 $C_3$-$C_{10}$cycloalkyl groups, or is a polycyclic alkyl group containing 7 to 10 carbon atoms, phenyl($C_1$-$C_5$)alkyl or phenyl($C_1$-$C_5$)alkyl which is mono- or disubstituted at the phenyl nucleus by halogen, trifluoromethyl, methoxy or ethoxy.

Alkyl and alkoxy groups and substituents $R_1$ to $R_4$ may be straight chain or branched. Examples of such groups are therefore methyl, methoxy, ethyl, propyl, isopropyl, n-butyl, isobutyl, sec-butyl, tert-butyl, n-pentyl, n-hexyl, n-heptyl, n-octyl, n-nonyl, n-decyl and the isomers thereof.

Within the scope of the present invention, halogen is preferably F, Cl and Br, most preferably F and Cl.

On account of their activity as pesticides, preferred compounds of formula I are those wherein $R_1$ is hydrogen, halogen, $C_1$-$C_{10}$alkyl, $C_1$-$C_5$alkoxy, $C_1$-$C_5$alkoxy which is substituted by 1 to 7 halogen atoms, or is $C_1$-$C_5$alkylthio;

$R_2$ is hydrogen, halogen, $C_1$-$C_{10}$alkyl or $C_1$-$C_5$alkoxy;

$R_3$ is hydrogen, $C_1$-$C_{10}$alkyl, haogen, phenoxy or phenoxy which is mono- or disubstituted by a member selected from the group consisting of halogen, trifluoromethyl and cyano, or is phenylthio, pyridyloxy or pyridyloxy which is mono- or disubstituted by a member selected from the group consisting of halogen and trifluoromethyl; and $R_4$ is $C_1$-$C_{10}$alkyl, alkoxyalkyl containing a total of 2 to 10 carbon atoms, $C_3$-$C_{10}$cycloalkyl, $C_3$-$C_{10}$cycloalkylmethyl, or $C_3$-$C_{10}$cycloalkyl which is substituted by a $C_1$-$C_3$alkyl group.

On account of their biological activity, further valuable compounds of formula I are those wherein $R_1$ is hydrogen, fluorine, chlorine, $C_1$-$C_4$alkyl, methoxy, ethoxy, trifluoromethoxy or $C_1$-$C_3$alkylthio;

$R_2$ is hydrogen, fluorine, chlorine, $C_1$-$C_4$alkyl, methoxy or ethoxy;

$R_3$ is hydrogen, $C_1$-$C_4$alkyl, fluorine, chlorine, phenoxy, phenylthio, phenoxy which is mono- or disubstituted by chlorine and/or trifluoromethyl, or is pyridyloxy or pyridyloxy which is mono- or disubstituted by a member selected from the group consisting of fluorine, chlorine and trifluoromethyl; and $R_4$ is $C_1$-$C_8$alkyl, alkoxyalkyl containing a total of 2 to 7 carbon atoms, $C_3$-$C_8$cylcoalkyl, $C_3$-$C_6$cycloalkylmethyl, methyl($C_3$-$C_6$)-cycloalkyl, phenyl($C_1$-$C_4$)alkyl or phenyl($C_1$-$C_4$)alkyl which is mono- or disubstituted at the phenyl nucleus by chlorine, trifluoromethyl or methoxy;

as well as those compounds of formula I, wherein $R_1$ is hydrogen, fluorine, chlorine, $C_2$-$C_4$alkyl or methoxy;

$R_2$ is hydrogen, chlorine, $C_3$-$C_4$alkyl or methoxy;

$R_3$ is methyl, ethyl, isopropyl, chlorine, phenoxy, phenoxy which is mono- or disubstituted by chlorine and/or trifluoromethyl, or is pyridyloxy or pyridyloxy which is mono- or disubstituted by chlorine and/or trifluoromethyl; and $R_4$ is $C_3$-$C_8$alkyl, $C_1$-$C_4$alkoxy($C_1$-$C_3$)alkyl, $C_3$-$C_6$-cycloalkyl, phenyl($C_1$-$C_4$)alkyl or phenyl($C_1$-$C_4$)alkyl which is substituted at the phenyl nucleus by a chlorine atom or a methoxy group.

Particularly preferred compounds of formula I are those wherein one of the radicals $R_1$, $R_2$ and $R_3$ is in the 4-position and the other two independently of each other are in the 2- and 6-positions. $R_4$ is preferably isopropyl and tert-butyl.

Still further preferred carbodiimides of formula I are those wherein $R_1$ and $R_2$ are attached to the phenyl radical in the 2- and 6-positions.

The compounds of formula I can be prepared by methods which are known per se. Thus, for example, a compound of formula I can be obtained by removing water or hydrogen sulfide from a compound of formula II

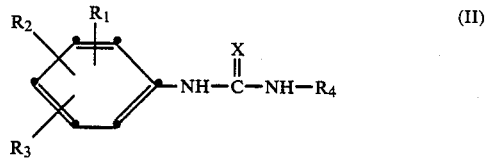

wherein $R_1$ to $R_4$ are as defined above and X is oxygen or sulfur. Such elimination reactions can be carried out in accordance with procedures known from the literature, e.g. with the aid of HgO, specific pyridinium salts, chloroacetates, cyanuric chloride, p-toluenesulfochloride or specific phosphate derivatives [T. Shibanuma, Chemistry Letters (1977), pp. 575–6; S. Kim, Tetrahedron Letters (1985), pp. 1661–1664; W. Weith, B.6 (1873) 1398; G. Amiard, Bull. Soc. chim. 1956, 1360].

The above process can preferably be carried out under normal pressure and in the presence of a preferably aprotic organic solvent or diluent. Examples of suitable solvents or diluents are: ethers and ethereal compounds such as diethyl ether, dipropyl ether, dibutyl ether, dioxane, dimethoxyethane and tetrahydrofuran; N,N-dialkylatedd carboxamides; aliphatic, aromatic and halogenated hydrocarbons, especially benzene, toluene, xylene, chloroform, methylene chloride, carbon tetrachloride and chlorobenzene; nitriles such as acetonitrile or propionitrile; and ketones, e.g. acetone, methyl ethyl ketone, methyl isopropyl ketone and methyl isobutyl ketone. The process is generally carried out at a temperature in the ranbge from −5° to +150° C., preferably from 10° to 50° C., e.g. at room temperature.

The carbodiimides of formula I can also be prepared in a manner known per se by reacting suitably substituted isocyanide dichlorides of formula III with a salt of the respective desired primary amine of formula IV (q.v. U.S. Patent Specification No. 3,231,610):

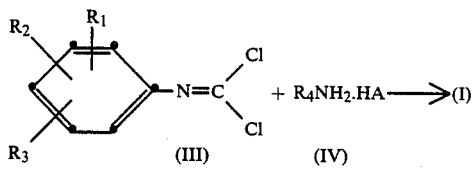

in which formulae III and IV the radicals $R_1$ to $R_4$ are as defined above and A is an anion, e.g. $Cl^\ominus$. Suitable primary amine salts for this reaction are e.g. the hydrohalides. The reaction is preferably carried out in the presence of an inert organic solvent with a relatively high boiling point, e.g. chlorinated benzenes, nitrobenzene, dimethylacetamide or tetramethylenesulfone. Examples of further suitable solvents are: high boiling aliphatic, cycloaliphatic and aromatic hydrocarbons such as p-chlorobromobenzene, 1-chloronaphthalene or halogenated xylenes. In general, the reaction is preferably carried out at a temperature in the range form 80° to 200° C.

The starting materials of formulae II, III and IV are known and can be obtained in accordance with known procedures (q.v. Belgian Patent Specification No. 863,078, German Patent Application No. 1 094 737 and U.S. Patent Specification No. 3,932,507).

The use of N,N'-diphenylcarbodiimides as acaricides, in particular as ectoparasiticides, is known from German Offenlegungsschrift No. 2 553 270. The use of substituted N-benzyl-N'-alkylcarbodiimides as insecticides is described in Japanese Patent Publication No. 5 0069 226. U.S. Patent Specification No. 3,231,610 also relates to substituted carbodiimides having herbicidal and insecticial properties. In addition to N,N'-dialkylcarbodiimides and N,N'-diphenylcarbodiimides, the general formula indicated in said U.S. patent specification also comprises specific N-phenyl-N'-alkylcarbodiimides; however, in the cited U.S. patent specification only chlorine- or nitro-substituted N,N'-diphenylcarbodiimides are specifically disclosed, but not N-phenyl-N'-alkylcarbodiimides.

In contradistinction thereto, the substituted N-phenyl-N'-alkyl-carbodiimides of the present invention are therefore novel compounds which, while being well tolerated by plants and having low mammalian toxicity to warm-blooded animals, surprisingly possess a pronounced activity for controlling insects and representatives of the order Acarina that attack plants and animals.

In particular, the compounds of formula I are suitable for controlling insects of the orders: Lepidoptera, Coleoptera, Homoptera, Heteroptera, Diptera, Thysanoptera, Orthoptera, Anoplura, Siphonaptera, Mallophaga, Thysanura, Isoptera, Psocoptera and Hymenoptera, as well as representatives of the order Acarina, in particular plant-destructive acarids, e.g. spider-mites.

The good pesticidal activity of the compounds of formula I of the invention corresponds to a mortality of at least 50–60% of the above pests.

In addition to their very effective action against flies, e.g. *Musca domestica,* and mosquito larvae, the compounds of formula I are particularly suitable for controlling plant-destructive feeding insects in ornamentals and crops of useful plants, especially in cotton (e.g. against *Spodoptera littoralis* and *Heliothis virescens*) and in crops of vegetables (e.g. against *Leptinotarsa decemlineata* and *Pieris brassicae*). The larvicidal and ovicidal action of the compounds of formula I is to be particularly highlighted. If compounds of formula I are ingested by adult insect stages with the feed, then a diminished oviposition and/or reduced hatching rate is observed in many insects, especially in Coleoptera, e.g. *Anthonomus grandis.*

The compounds of formula I can also be used for controlling ectoparasites such as *Lucilia sericata,* and ticks, in domestic animals and productive livestock, e.g. by treating animals, cowsheds, barns, stables etc., and pastures.

The activity of the compounds of formula I and of the compositions containing them can be substantially broadened and adapted to prevailing circumstances by addition of other insecticides and/or acaricides. Examples of suitable additives include: organophosphorus compounds, nitrophenols and derivatives thereof, formamidines, ureas, carbamates, pyrethroids, chlorinated hydrocarbons, and *Bacillus thuringiensis* preparations.

The compounds of formula I are used in unmodified form, or preferably together with the adjuvants conventionally employed in the art of formulation, and are therefore formulated in known manner to emulsifiable concentrates, directly sprayable or dilutable solutions, dilute emulsions, wettable powders, soluble powders, dusts, granulates, and also encapsulations in e.g. polymer substances. As with the nature of the compositions, the method of application such as spraying, atomising, dusting, scattering or pouring, are chosen in accordance with the intended objectives and the prevailing circumstances.

The formulations, i.e. the compositions, preparations or mixtures containing the compound (active ingredient) of formula I or combinations thereof with other insecticides or acaricides, and, where appropriate, a solid or liquid adjuvant, are prepared in known manner, e.g. by homogeneously mixing and/or grinding the active ingredients with extenders, e.g. solvents, solid carriers and, in some cases, surface-active compounds (surfactants).

Suitable slvents are: aromatic hydrocarbons, preferably the fractions containing 8 to 12 carbon atoms, e.g. xylene mixtures or substituted naphthalenes, phthalates such as dibutyl phthalate or dioctyl phthalate, aliphatic hydrocarbons such as cyclohexane or paraffins, alcohols and glycols and their ethers and esters, such as ethanol, ethylene glycol monomethyl or monoethyl ether, ketones such as cyclohexanone, strongly polar solvents such as N-methyl-2-pyrrolidone, dimethyl sulfoxide or dimethylformamide, as well as vegetable oils or epoxidised vegetable oils such as epoxidised coconut oil or soybean oil; or water.

The solid carriers used e.g. for dusts and dispersible powders are normally natural mineral fillers such as calcite, talcum, kaolin, montmorillonite or attapulgite. In order to improve the physical properties it is also possible to add highly dispersed silicic acid or highly dispersed absorbent polymers. Suitable granulated adsorptive carriers are porous types, for example pumice, broken brick, sepiolite or bentonite; and suitable non-sorbent carriers are materials such as calcite or sand. In addition, a great number of pregranulated materials of inorganic or organic nature can be used, e.g. especially dolomite or pulverised plant residues.

Depending on the nature of the compound of formula I to be formulated, or of combinations thereof with other insecticides or acaricides, suitable surface-active compounds are nonionic, cationic and/or anionic surfactants having good emulsifying, dispersing and wetting properties. The term "surfactants" will also be understood as comprising mixtures of surfactants.

Suitable anionic surfactants can be both water-soluble soaps and water-soluble synthetic surface-active compounds.

Suitable soaps are the alkali metal salts, alkaline earth metal salts or unsubstituted or substituted ammonium salts of higher fatty acids ($C_{10}$–$C_{22}$), e.g. the sodium or potassium salts of oleic or stearic acid, or of natural fatty acid mixtures which can be obtained, e.g. from coconut oil or tallow oil. Further suitable surfactants are also the fatty acid methyltaurin salts as well as modified and unmodified phospholipids.

More frequently, however, so-called synthetic surfactants are used, especially fatty sulfonates, fatty sulfates, sulfonated benzimidazole derivatives or alkylarylsulfonates.

The fatty sulfonates or sulfates are usually in the form of alkali metal salts, alkaline earth metal salts or unsubstituted or substituted ammonium salts and contain a $C_8$–$C_{22}$alkyl radical which also includes the alkyl moiety of acyl radicals, e.g. the sodium or calcium salt of lignosulfonic acid, of dodecylsulfate, or of a mixture of fatty alcohol sulfates obtained from natural fatty acids. These compounds also comprise the salts of sulfuric acid esters and sulfonic acids of fatty alcohol/ethylene oxide adducts. The sulfonated benzimidazole derivatives preferably contain 2 sulfonic acid groups and one fatty acid radical containing about 8 to 22 carbon atoms. Examples of alkylarylsulfonates are the sodium, calcium or triethanolamine salts of dodecylbenzenesulfonic acid, dibutylnaphthalenesulfonic acid, or of a naphthalenesulfonic acid/-formaldehyde condensation product. Also suitable are corresponding phosphates, e.g. salts of the phosphoric acid ester of an adduct of p-nonylphenol with 4 to 14 moles of ethylene oxide.

Non-ionic surfactants are preferably polyglycol ether derivatives of aliphatic or cycloaliphatic alcohols, or saturated or unsaturated fatty acids and alkylphenols, said derivatives containing 3 to 30 glycol ether groups and 8 to 20 carbon atoms in the (aliphatic) hydrocarbon moiety and 6 to 18 carbon atoms in the alkyl moiety of the alkylphenols.

Further suitable non-ionic surfactants are the water-soluble adducts of polyethylene oxide with polypropylene glycol, ethylenediaminopolypropylene glycol and alkylpolypropylene glycol containing 1 to 10 carbon atoms in the alkyl chain, which adducts contain 20 to 250 ethylene glycol ether groups and 10 to 100 propylene glycol ether groups. These compounds usually contain 1 to 5 ethylene glycol units per propylene glycol unit.

Representative examples of non-ionic surfactants are nonylphenolpolyethoxyethanols, castor oil polyglycol ethers, polypropylene/-polyethylene oxide adducts, tributylphenoxypolyethanol, polyethylene glycol and octylphenoxypolyethoxyethanol. Fatty acid esters of polyoxyethylene sorbitan, e.g. polyoxyethylene sorbitan triolate, are also suitable non-ionic surfactants.

Cationic surfactants are preferably quaternary ammonium salts which contain, as N-substituent, at least one $C_8$–$C_{22}$alkyl radical and, as further substituents, unsubstituted or halogenated lower alkyl, benzyl or hydroxy-lower alkyl radicals. The salts are preferably in the form of halides, methylsulfates or ethylsulfates, e.g. stearyltrimethylammonium chloride or benzyldi(2-chloroethyl)ethylammonium bromide.

The surfactants customarily employed in the art of formulation are described e.g. in "McCutcheon's Detergents and Emulsifiers Annual", MC Publishing Corp. Ridgewood, N.J., 1979; Dr. Helmut Stache, "Tensid Taschenbuch" (Handbook of Surfactants), Carl Hanser Verlag, Munich/Vienna, 1981.

The pesticidal compositions usually contain 0.1 to 99%, preferably 0.1 to 95%, of a compound of formula I or combinaton thereof with other insecticides or acaricides, 1 to 99.9% of a solid or liquid adjuvant, and 0 to 25%, preferably 0.1 to 20%, of a surfactant.

Whereas commercial products are preferably formulated as concentrates, the end user will normally employ dilute formulations of substantially lower concentration.

The compositions may also contain further ingredients, such as stabilisers, antifoams, viscosity regulators, binders, tackifiers as well as fertilisers or other active ingredients in order to obtain special effects.

EXAMPLE 1

Preparation of N-[2,6-dimethyl-4-(3,5-dichloro-2-pyridyloxy)phenyl]-N'-tert-butylcarbodiimide A reaction vessel is charged with 16.6 g of N-[2,6-dimethyl-4-(3,5-dichloro-2-pyridyloxy)phenyl]-N'-tert-butylthiourea and 12.8 g of 2-chloro-1-methylpyridinium iodide in 150 ml of acetonitrile. With stirring, a solution of 8.4 g of triethylamine in 80 ml of acetonitrile is added dropwise at room temperature. The reaction mixture is subsequently stirred for 2 hours at 80° C. and then concetrated by rotary evaporation at 50° C. 150 ml of hexane are added to the residue and the resultant solution is filtered. The hexane phase is washed with three 30 ml portions of cold water, dried over sodium sulfate and filtered. The filtrate is concentrated by evaporation, affording the title compound of the formula

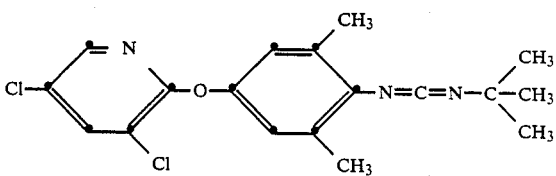

as a clear pale yellow oil which crystallises on standing and has a melting point of 69°–71° C. (compound 1).

The following compounds of formula I are also obtained in accordance with the procedure described above:

| Compound | $R_1$ | $R_2$ | $R_3$ | $R_4$ | Physical data |
|---|---|---|---|---|---|
| 2 | 2-CH$_3$ | 6-CH$_3$ | 4-O–C$_6$H$_5$ | –C$_4$H$_9$(t) | $n_{20}^D = 1.5764$ |
| 3 | 2-C$_3$H$_7$(i) | H | 6-C$_3$H$_7$(i)–C$_6$H$_4$ | –C$_4$H$_9$(t) | white, viscous substance which liquefies at room temperature |
| 4 | 2-C$_3$H$_7$(i) | 6-C$_3$H$_7$(i) | 4-O–C$_6$H$_5$ | –C$_4$H$_9$(t) | m.p. 45–46° C. |
| 5 | 3-Cl | H | 4-Cl | –C$_4$H$_9$(t) | $n_{21}^D = 1.5613$ |
| 6 | 2-Cl | H | 4-Cl | –C$_4$H$_9$(t) | $n_{20}^D = 1.5895$ |
| 7 | H | H | 4-OCH$_3$-2-CF$_3$-pyridyl | –C$_4$H$_9$(t) | m.p. 51–53° C. |
| 8 | 6-C$_4$H$_9$(s) | 2-C$_2$H$_5$ | 4-O–C$_6$H$_5$ | –C$_4$H$_9$(t) | $n_{22}^D = 1.5575$ |
| 9 | 2-C$_3$H$_7$(i) | 6-C$_3$H$_7$(i) | H | 4-Cl-C$_6$H$_4$–C(CH$_3$)$_2$– | $n_{24}^D = 1.5685$ |
| 10 | H | H | 4-O–C$_6$H$_5$ | –C$_4$H$_9$(t) | $n_{24}^D = 1.5756$ |
| 11 | H | H | 4-O–C$_6$H$_5$ | C$_6$H$_5$ | $n_{24}^D = 1.5952$ |

-continued

| Compound | $R_1$ | $R_2$ | $R_3$ | $R_4$ | Physical data |
|---|---|---|---|---|---|
| 12 | 2-$C_3H_7$(i) | H | 4-O-C₆H₄-CF₃ | —$C_4H_9$(t) | $n_{20}^D = 1.5300$ |
| 13 | 2-$CH_3$ | 6-$CH_3$ | 4-O-C₆H₄-Cl | —$C_4H_9$(t) | $n_{20}^D = 1.5815$ |
| 14 | 2-$CH_3$ | 6-$CH_3$ | 4-O-C₆H₄-CF₃ | —$C_4H_9$(t) | $n_{20}^D = 1.5374$ |
| 15 | 2-$CH_3$ | 6-$CH_3$ | 4-O-C₆H₄- | —$CH_2$—$C_4H_9$(t) | $n_{20}^D = 1.5720$ |
| 16 | 2-$CH_3$ | 6-$CH_3$ | 4-O-C₆H₄-CF₃ | cyclohexyl(H, CH₃) | $n_{20}^D = 1.5505$ |
| 17 | H | H | 4-S-C₆H₅ | —$C_4H_9$(t) | $n_{20}^D = 1.6142$ |
| 18 | 2-$CH_3$ | 4-Cl | H | —$CH_3$ | $n_{20}^D = 1.6230$ |
| 19 | 2-$CH_3$ | 6-$CH_3$ | 4-O-C₆H₃(Cl)(CF₃) | —$C_4H_9$(t) | $n_{20}^D = 1.5460$ |

-continued

| Compound | R₁ | R₂ | R₃ | R₄ | Physical data |
|---|---|---|---|---|---|
| 20 | 2-CH₃ | 6-CH₃ | 4-O-pyridyl(3-CF₃, 5-Cl) | —C₃H₇(i) | m.p. 50-52° C. |
| 21 | 2-CH₃ | 6-CH₃ | 4-O-pyridyl(3-CF₃, 5-Cl) | —C₄H₉(t) | m.p. 65-68° C. |
| 22 | 6-CH₃ | 2-CH₃ | 4-O-phenyl | phenyl(H) | $n_{27}^D = 1.5905$ |
| 23 | 6-OCH₃ | 2-OCH₃ | 4-O-phenyl(2-CN, 3-CF₃) | —C₄H₉(t) | m.p. 61-64° C. |
| 24 | 2-CH₃ | 6-CH₃ | | —C₄H₉(t) | m.p. 67-68° C. |
| 25 | H | 2-CH₃ | 4-O-phenyl(4-CF₃) | C₄H₉(t) | $n_{21}^D = 1.5350$ |
| 26 | 2-C₄H₉(s) | 6-C₂H₅ | 4-O-phenyl | phenyl(CH₃, H) | $n_{21}^D = 1.5672$ |
| 27 | 2-OCH₃ | 6-OCH₃ | H | phenyl(H) | m.p. 57-60° C. |

-continued

| Compound | R₁ | R₂ | R₃ | R₄ | Physical data |
|---|---|---|---|---|---|
| 28 | 2-CH₃ | 6-CH₃ | 4-O—, 3-Cl, 5-Cl pyridyl | —(CH₂)₃—O—(CH₂)₃—CH₃ | $n_{21}^D = 1.5726$ |
| 29 | 2-CH₃ | 6-CH₃ | 4-O—, 3-Cl, 5-CF₃ pyridyl | —(CH₂)₃—O—(CH₂)₃—CH₃ | $n_{21}^D = 1.5355$ |
| 30 | 2-C₃H₇(i) | H | 6-C₃H₇(i) | 4-CH₃-cyclohexyl | $n_{21}^D = 1.5388$ |
| 31 | 2-C₄H₉(s) | 6-C₂H₅ | H | cyclohexyl | $n_{21}^D = 1.5721$ |
| 32 | 2-C₃H₇(i) | 6-C₃H₇(i) | H | —C(CH₃)₂—CH₂—C(CH₃)₂—CH₃ | $n_{21}^D = 1.5177$ |
| 33 | 2-C₃H₇(i) | 6-C₃H₇(i) | H | —CH—[(CH₂)₆—CH₂] | $n_{21}^D = 1.5743$ |
| 34 | 4-CH₃ | H | 2-CH₃ | —C₄H₉(i) | $n_{21}^D = 1.5340$ |
| 35 | 2-CH₃ | H | 6-CH₃ | —C₃H₇(i) | $n_{23}^D = 1.5459$ |
| 36 | 2-CH₃ | H | 6-CH₃ | —C₄H₉(i) | $n_{23}^D = 1.5354$ |
| 37 | 2-CH₃ | H | 6-CH₃ | —C₄H₉(s) | $n_{24}^D = 1.5424$ |
| 38 | 2-Cl | H | 4-Cl | —C₄H₉(i) | $n_{23}^D = 1.5650$ |
| 39 | 2-Cl | H | 4-Cl | —C₃H₇(i) | $n_{22}^D = 1.5826$ |
| 40 | 2-C₂H₅ | H | 6-C₄H₉(s) | —C₄H₉(i) | $n_{22}^D = 1.5230$ |
| 41 | 6-C₃H₇(i) | H | 2-C₂H₅ | —C₃H₇(i) | $n_{23}^D = 1.5300$ |
| 42 | 2-C₃H₇(i) | H | 6-CH₃ | —C₄H₉(i) | $n_{25}^D = 1.5261$ |
| 43 | 2-C₃H₇(i) | H | 6-C₂H₅ | —C₄H₉(i) | $n_{23}^D = 1.5256$ |
| 44 | 2-C₃H₇(i) | H | 6-C₃H₇(i) | —C₃H₇(i) | $n_{23}^D = 1.5293$ |
| 45 | 2-CH₃ | H | 4-CH₃ | —C₃H₇(i) | $n_{22}^D = 1.5450$ |

-continued

| Compound | $R_1$ | $R_2$ | $R_3$ | $R_4$ | Physical data |
|---|---|---|---|---|---|
| 46 | 2-C$_2$H$_5$ | H | 6-C$_4$H$_9$(s) | cyclopropyl | $n_{22}^D = 1.5498$ |
| 47 | 2-C$_2$H$_5$ | H | 6-C$_4$H$_9$(s) | cyclopentyl (H) | $n_{22}^D = 1.5464$ |
| 48 | 2-S—C$_3$H$_7$(i) | H | 6-Cl | —C$_4$H$_9$(t) | $n_{21}^D = 1.5805$ |
| 49 | 4-OCF$_3$ | H | H | —C$_4$H$_9$(t) | $n_{22}^D = 1.4780$ |
| 50 | 2-C$_3$H$_7$(i) | 6-C$_3$H$_7$(i) | 4-O-phenyl | —(CH$_2$)$_3$—O—(CH$_2$)$_3$—CH$_3$ | $n_{23}^D = 1.5452$ |
| 51 | 2-C$_3$H$_7$(i) | 6-C$_3$H$_7$(i) | 4-O-phenyl | —(CH$_2$)$_3$—OCH$_3$ | $n_{23}^D = 1.5589$ |
| 52 | 2-C$_3$H$_7$(i) | 6-C$_3$H$_7$(i) | H | cyclohexyl-CH$_2$— | $n_{21}^D = 1.5408$ |
| 53 | 2-C$_2$H$_5$ | 6-C$_4$H$_9$(s) | H | 4-methylcyclohexyl (H) | $n_{21}^D = 1.5402$ |
| 54 | 2-C$_2$H$_5$ | 6-C$_4$H$_9$(s) | 4-O-phenyl | —C(CH$_3$)$_2$—CH$_2$—C(CH$_3$)$_3$ | $n_{21}^D = 1.5482$ |

-continued

| Compound | R₁ | R₂ | R₃ | R₄ | Physical data |
|---|---|---|---|---|---|
| 55 | 2-CH₃ | 6-CH₃ | 4-O-pyridyl-3,5-diCl (N, 4-O, 3-Cl, 5-Cl) | -C(CH₃)₂-CH₂-C(CH₃)₃ | $n_{21}^D = 1.5730$ |
| 56 | 2-CH₃ | 6-CH₃ | 4-O-pyridyl-3,5-diCl | phenyl (H) | m.p. 41–44° C. |
| 57 | H | 2-CH₃ | 4-S-phenyl-Cl | -C₄H₉(t) | m.p. 37–38° C. |
| 58 | 2-C₃H₇(i) | H | 4-O-phenyl-CF₃ | -CH(CH₃)-CH₂-OCH₃ | $n_{21}^D = 1.5329$ |
| 59 | H | 2-C₃H₇(i) | 4-O-pyridyl | -CH₂-CH₂-CH₂-O-C₄H₉(n) | $n_{21}^D = 1.5548$ |
| 60 | H | 2-C₃H₇(i) | 4-O-pyridyl | -C₄H₉(t) | m.p. 33–35° C. |
| 61 | 4-C₄H₉(t) | H | H | -C₄H₉(t) | $n_{21}^D = 1.1538$ |
| 62 | 4-C₄H₉(t) | H | H | -C(CH₃)₂-CH₂-C(CH₃)₃ | $n_{21}^D = 1.5212$ |

-continued

| Compound | $R_1$ | $R_2$ | $R_3$ | $R_4$ | Physical data |
|---|---|---|---|---|---|
| 63 | 4-$C_4H_9$(t) | H | H | phenyl | $n_{21}^D = 1.5485$ |
| 64 | H | 2-$C_3H_7$(i) | 4-$CF_3$-phenyl | —CH($C_3H_7$(i))$_2$ | $n_{21}^D = 1.5249$ |
| 65 | 4-$CH_3$ | 2-$CH_3$ | 3-$CF_3$-(6-methylpyridin-2-yl) | —$C_4H_9$(t) | $n_{21}^D = 1.5217$ |
| 66 | 2-$CH_3$ | 6-$CH_3$ | 4-(6-methylpyridin-2-yl) | —$C_4H_9$(t) | $n_{21}^D = 1.5768$ |
| 67 | 2-$CH_3$ | 6-$CH_3$ | 4-(6-methylpyridin-2-yl) | —CH($CH_3$)—$CH_2$—$OCH_3$ | $n_{21}^D = 1.5792$ |
| 68 | 2-$CH_3$ | 6-$CH_3$ | 4-(6-methylpyridin-2-yl) | phenyl | $n_{21}^D = 1.5989$ |
| 69 | H | 2-$C_3H_7$(i) | 6-$C_3H_7$(i) | —CH($C_3H_7$(i))$_2$ | $n_{21}^D = 1.5200$ |

-continued

| Compound | $R_1$ | $R_2$ | $R_3$ | $R_4$ | Physical data |
|---|---|---|---|---|---|
| 70 | H | 2-C$_3$H$_7$(i) | 6-C$_3$H$_7$(i) | —CH(cyclopropyl)$_2$ | $n_{21}^D = 1.5409$ |
| 71 | 2-CH$_3$ | 6-CH$_3$ | 4-O-(3,5-dichloropyridin-2-yl) | —C(CH$_3$)$_2$—C$_2$H$_5$ | $n_{21}^D = 1.5852$ |
| 72 | 2-CH$_3$ | 6-CH$_3$ | 4-O-(3,5-dichloropyridin-2-yl) | —CH(cyclopropyl)$_2$ | $n_{21}^D = 1.6000$ |
| 73 | 2-CH$_3$ | 6-CH$_3$ | 4-O-phenyl | —CH(C$_3$H$_7$(i))$_2$ | $n_{21}^D = 1.5662$ |
| 74 | 2-CH$_3$ | 6-CH$_3$ | 4-O-(3,5-dichloropyridin-2-yl) | —CH$_2$-(4-H-cyclohexyl) | $n_{21}^D = 1.5950$ |
| 75 | 2-CH$_3$ | 6-CH$_3$ | 4-O-phenyl | —CH(CH$_3$)-(4-H-cyclohexyl) | $n_{21}^D = 1.5820$ |
| 76 | 2-C$_3$H$_7$(i) | H | H | —C$_4$H$_9$(i) | $n_{23}^D = 1.5359$ |
| 77 | 2-CH$_3$ | H | 6-C$_2$H$_5$ | —C$_3$H$_7$(i) | $n_{23}^D = 1.5396$ |

-continued

| Compound | R₁ | R₂ | R₃ | R₄ | Physical data |
|---|---|---|---|---|---|
| 78 | H | 6-C₂H₅ | 2-CH₃<br>4-O—⬡ | —C₄H₉(t) | $n_{23}^D = 1.5296$ |
| 79 | 2-C₃H₇(i) | 6-C₃H₇(i) | 4-O—⬡ | —(CH₂)₃—O—C₂H₅ | $n_{23}^D = 1.5527$ |
| 80 | 2-C₃H₇(i) | 6-C₃H₇(i) | 4-O—⬡ | —(CH₂)₃—O—C₃H₇(i) | $n_{23}^D = 1.5473$ |
| 81 | 2-C₃H₇(i) | 6-C₃H₇(i) | 4-O—⬡ | CH₃—C(CH₃)(CH₃)—CH₂—C(CH₃)—CH₃ | $n_{23}^D = 1.5466$ |
| 82 | 2-C₃H₇(i) | 6-C₃H₇(i) | 4-O—⬡ | cyclopentyl | $n_{23}^D = 1.5680$ |
| 83 | 2-C₃H₇(i) | 6-C₃H₇(i) | 4-O—⬡ | cyclohexyl | $n_{23}^D = 1.5702$ |
| 84 | 2-C₃H₇(i) | 6-C₃H₇(i) | 4-O—⬡ | —CH₂—(cyclopropyl) | $n_{23}^D = 1.5740$ |
| 85 | 2-C₃H₇(i) | 6-C₃H₇(i) | 4-O—⬡ | —CH₂—(cyclohexyl) | $n_{23}^D = 1.5663$ |
| 86 | 2-C₃H₇(i) | 6-C₃H₇(i) | 4-O—⬡ | —CH₂—CH—[(CH₂)₆—CH₂] | $n_{23}^D = 1.5657$ |

-continued

| Compound | $R_1$ | $R_2$ | $R_3$ | $R_4$ | Physical data |
|---|---|---|---|---|---|
| 87 | 2-$C_3H_7$(i) | 6-$C_3H_7$(i) | H | —$CH_2$—CH—($CH_2)_6$—$CH_2$ (cyclic) | $n_{23}^D = 1.5440$ |
| 88 | 2-$C_2H_5$ | 6-$C_2H_5$ | H | —$C_3H_6$(i) | $n_{23}^D = 1.5358$ |
| 89 | 2-$C_2H_5$ | 6-$C_2H_5$ | H | —$C_4H_9$(t) | $n_{23}^D = 1.5294$ |
| 90 | 2-$C_2H_5$ | 6-$C_2H_5$ | 4-O-phenyl | —$C_2H_7$(i) | $n_{25}^D = 1.572$ |
| 91 | 2-$C_2H_5$ | 6-$C_2H_5$ | 4-O-phenyl | —$C_4H_9$(t) | $n_{23}^D = 1.5670$ |
| 92 | 2-$C_3H_7$(i) | 6-$C_3H_7$(i) | 4-O-phenyl | —C($CH_3)_2$—$C_2H_5$ | $n_{23}^D = 1.5550$ |
| 93 | 2-$C_2H_5$ | 6-$C_2H_5$ | 4-O-phenyl | cyclopentyl-H | $n_{23}^D = 1.5844$ |
| 94 | 2-$C_2H_5$ | 6-$C_2H_5$ | 4-O-phenyl | —$C_4H_9$(s) | $n_{23}^D = 1.5703$ |
| 95 | 2-$C_2H_5$ | 6-$C_2H_5$ | 4-O-phenyl | —C($CH_3)_2$—$C_2H_5$ | $n_{23}^D = 1.5650$ |

-continued

| Compound | R₁ | R₂ | R₃ | R₄ | Physical data |
|---|---|---|---|---|---|
| 96 | 2-CH₃ | 6-CH₃ | 4-O-C₆H₄ | 2,6-di-iPr-C₆H₃ (H at 4) | $n_{21}^D = 1.5643$ |
| 97 | 2-CH₃ | 6-CH₃ | 4-O-C₆H₄ | cyclopentyl | $n_{21}^D = 1.5951$ |
| 98 | 2-C₃H₇(i) | 6-C₃H₇(i) | 4-O-C₆H₄ | CH[C₃H₇(i)]₂ | $n_{21}^D = 1.5510$ |
| 99 | 2-C₃H₇(i) | 6-C₃H₇(i) | 4-O-C₆H₄ | dicyclopropylmethyl | $n_{21}^D = 1.5531$ |
| 100 | 2-C₃H₇(i) | 6-C₃H₇(i) | 4-O-C₆H₄ | 2,6-di-iPr-C₆H₃ (H at 4) | $n_{21}^D = 1.5531$ |
| 101 | 2-C₃H₇(i) | 6-C₃H₇(i) | 4-O-C₆H₄ | —CH(CH₃)-C₆H₄-H | $n_{21}^D = 1.5640$ |

-continued

| Compound | R₁ | R₂ | R₃ | R₄ | Physical data |
|---|---|---|---|---|---|
| 102 | 2-C₂H₅ | 6-C₄H₉(s) | 4-O—⌬ | —CH(cyclopropyl)₂ | $n_{21}^D = 1.5698$ |
| 103 | 2-CH₃ | 6-CH₃ | 4-O—(3,5-dichloropyridin-2-yl) | —CH(CH₃)(phenyl) | $n_{21}^D = 1.5938$ |
| 104 | 2-CH₃ | 6-CH₃ | 4-O—(3,5-dichloropyridin-2-yl) | 2,6-di-C₃H₇(i)-phenyl (H at 4) | $n_{21}^D = 1.5879$ |
| 105 | 2-CH₃ | 6-CH₃ | 4-O—(3,5-dichloropyridin-2-yl) | 2,6-di-C₃H₇(i)-phenyl (H at 4) | $n_{21}^D = 1.5742$ |
| 106 | 2-CH₃ | 4-O—CF₂CHF₂ | 6-CH₃ | —C₄H₉(t) | $n_{21}^D = 1.4820$ |
| 107 | 2-CH₃ | 6-CH₃ | 4-O—(4-fluorophenyl) | —C₄H₉(t) | $n_{24}^D = 1.5618$ |
| 108 | 2-CH₃ | 6-CH₃ | 4-O—pyridyl | —C(CH₃)₂—(4-chlorophenyl) | $n_{21}^D = 1.6119$ |

-continued
| Compound | R₁ | R₂ | R₃ | R₄ | Physical data |
|---|---|---|---|---|---|
| 109 | 2-C₃H₇(i) | 6-C₃H₇O | H |  | $n_{21}^D = 1.5570$ |
| 110 | 2-C₃H₇(i) | 6-C₃H₇O | H |  | $n_{21}^D = 1.5532$ |
| 111 | 2-CH₃ | 6-CH₃ |  | —C₄H₉(i) | $n_{21}^D = 1.5515$ |
| 112 | 2-CH₃ | 6-CH₃ |  | —C₃H₇(i) | $n_{22}^D = 1.5592$ |
| 113 | H | 2-C₃H₇(i) |  |  | $n_{21}^D = 1.5550$ |
| 114 | 2-CH₃ | 6-CH₃ |  | —C(CH₃)₂—₂H₅ | $n_{21}^D = 1.5538$ |
| 115 | 2-CH₃ | 6-CH₃ | 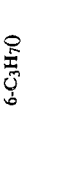 |  | $n_{21}^D = 1.5739$ |

-continued

| Compound | R₁ | R₂ | R₃ | R₄ | Physical data |
|---|---|---|---|---|---|
| 116 | H | 4-O—CF₂CHF₂ | 2-C₃H₇(i) | —CH(CH₃)—CH₂—CH₂—phenyl | $n_{21}^D = 1.5177$ |
| 117 | 2-C₃H₇(i) | 4-O—CF₂CHF₂ | H | cyclopropyl-CH₂ | $n_{21}^D = 1.5100$ |
| 118 | 2-C₃H₇(i) | H | 4-O-phenyl-4-CF₃ | —CH(CH₃)—CH₂—CH₂—phenyl | $n_{21}^D = 1.5572$ |
| 119 | 2-C₃H₇(i) | 6-C₃H₇(i) | H | —CH(CH₃)—CH₂—CH₂—phenyl | $n_{21}^D = 1.5561$ |
| 120 | 2-CH₃ | 6-CH₃ | 4-O-phenyl | —C(CH₃)₂—(3-Cl-phenyl) | $n_{21}^D = 1.6096$ |
| 121 | 2-CH₃ | 6-CH₃ | 4-O-phenyl | —CH(CH₃)—phenyl | $n_{21}^D = 1.6217$ |
| 122 | 2-CH₃ | 6-CH₃ | 4-O-phenyl | —C(CH₃)(CH₂—)(3-OCH₃,4-OCH₃-phenyl) | $n_{21}^D = 1.5982$ |
| 123 | 2-CH₃ | 6-CH₃ | 4-O-phenyl | —CH(CH₃)—CH₂—phenyl | $n_{21}^D = 1.6026$ |

-continued

| Compound | R$_1$ | R$_2$ | R$_3$ | R$_4$ | Physical data |
|---|---|---|---|---|---|
| 124 | 2-CH$_3$ | 6-CH$_3$ | 4-O–C$_6$H$_4$– | –CH$_2$–CH$_2$–CH$_2$–CH$_2$– (to phenyl) | $n_{21}^D = 1.5999$ |
| 125 | 2-CH$_3$ | 6-CH$_3$ | 4-O-(3,5-dichloropyridin-2-yl) | –CH(CH$_3$)–CH$_2$–CH$_2$– (to phenyl) | $n_{21}^D = 1.6094$ |
| 126 | 2-C$_2$H$_5$ | 6-CH$_3$ | 4-O-(3-Cl-5-CF$_2$CFCl$_2$-pyridin-2-yl) | –C$_4$H$_9$(t) | $n_{21}^D = 1.5520$ |
| 127 | 2-C$_3$H$_7$(i) | 6-C$_3$H$_7$(i) | H | 1-adamantyl | m.p. 93–95° C. |
| 128 | 2-C$_3$H$_7$(i) | 6-C$_3$H$_7$(i) | H | –C(CH$_3$)$_2$–C$_6$H$_5$ | $n_{21}^D = 1.5639$ |
| 129 | 2-C$_2$H$_5$ | 6-C$_2$H$_5$ | H | –C(CH$_3$)$_2$–C$_6$H$_5$ | $n_{24}^D = 1.5715$ |
| 130 | 2-C$_2$H$_5$ | 6-C$_4$H$_9$(s) | H | norbornyl | $n_{21}^D = 1.5518$ |
| 131 | 2-C$_2$H$_5$ | 6-C$_4$H$_9$(s) | H | 1-adamantyl | $n_{24}^D = 1.5618$ |
| 132 | 2-C$_2$H$_5$ | 6-C$_4$H$_9$(s) | H | –CH(CH$_3$)–C$_6$H$_5$ | $n_{24}^D = 1.5662$ |

-continued
| Compound | R₁ | R₂ | R₃ | R₄ | Physical data |
|---|---|---|---|---|---|
| 133 | 2-C₃H₇(i) | 6-C₃H₇(i) | H |  —CH₂—C(CH₃)₂— (4-O—C₂H₅-phenyl) | $n_{24}^D = 1.5550$ |
| 134 | 2-C₂H₅ | 6-C₂H₅ | H | 1-adamantyl | $n_{24}^D = 1.5724$ |
| 135 | 2-CH₃ | 6-C₃H₇(i) | H | 1-adamantyl | — |
| 136 | 2-CH₃ | 6-CH₃ | 4-O-(phenyl) | 1-adamantyl | — |
| 137 | 2-C₃H₇(i) | H | 4-O-(4-CF₃-phenyl) |  cyclohexyl with C₃H₇(i) and H | $n_{24}^D = 1.5382$ |
| 138 | 2-C₂H₅ | 6-C₄H₉(s) | H | 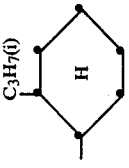 —CH(dicyclopropyl) | $n_{24}^D = 1.5409$ |
| 139 | 2-C₃H₇(i) | 6-C₃H₇(i) | H | 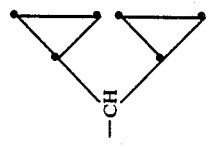 cyclohexyl with C₃H₇(i) and H | $n_{24}^D = 1.5351$ |
| 140 | 2-CH₃ | 6-CH₃ | 4-O-(phenyl) | 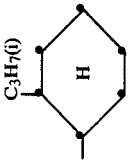 —CH(CH₃)(cyclopropyl) | $n_{24}^D = 1.5808$ |

-continued

| Compound | $R_1$ | $R_2$ | $R_3$ | $R_4$ | Physical data |
|---|---|---|---|---|---|
| 141 | 2-$C_3H_7$(i) | 6-$C_3H_7$(i) | 4-O-$C_6H_4$- | -C(CH$_3$)$_2$-C$_6$H$_4$-H | $n_{24}^D = 1.5615$ |
| 142 | 2-$C_2H_5$ | 6-$C_4H_9$(s) | 4-O-$C_6H_4$- | -CH(C$_3$H$_7$(i))-C$_6$H$_4$- | $n_{24}^D = 1.5614$ |
| 143 | 2-$C_2H_5$ | 6-$C_4H_9$(s) | 4-O-$C_6H_4$- | -C(CH$_3$)$_2$-C$_6$H$_4$-H | $n_{24}^D = 1.5635$ |
| 144 | 2-$CH_3$ | 6-$CH_3$ | 4-O-(3,5-Cl$_2$-pyridyl) | -CH(CH$_3$)-cyclopropyl | $n_{24}^D = 1.5970$ |
| 145 | 2-$CH_3$ | 6-$CH_3$ | 4-O-(3,5-Cl$_2$-pyridyl) | -C(CH$_3$)$_2$-C$_6$H$_4$-H | $n_{24}^D = 1.5892$ |
| 146 | 2-$C_2H_5$ | 6-$C_2H_5$ | 4-O-(3,5-Cl$_2$-pyridyl) | -$C_4H_9$(t) | $n_{24}^D = 1.5770$ |
| 147 | 2-$CH_3$ | 6-$CH_3$ | 4-O-(3-Cl-5-F-pyridyl) | -$C_4H_9$(t) | $n_{24}^D = 1.5720$ |

-continued

| Compound | R₁ | R₂ | R₃ | R₄ | Physical data |
|---|---|---|---|---|---|
| 148 | 2-CH₃ | 6-CH₃ | 4-O-C₆H₄ | 4-(CH₃)₂C-C₆H₄-H (cyclohexyl-like with C(CH₃)₂) | $n_{24}^D = 1.5790$ |
| 149 | 2-CH₃ | 6-C₂H₅ | 4-O-(3-Cl, 5-Cl, 6-CH₃-pyridin-2-yl) | —C₄H₉(t) | $n_{24}^D = 1.5820$ |
| 150 | 2-CH₃ | 6-CH₃ | 4-O-(3-Cl, 5-Cl, 6-CH₃-pyridin-2-yl) | —C₃H₇(i) | $n_{24}^D = 1.5983$ |
| 151 | 2-CH₃ | 6-CH₃ | 4-O-(3-Cl, 5-Cl, 6-CH₃-pyridin-2-yl) | cyclopentyl-H | m.p. 65–68° C. |
| 152 | 2-C₃H₇(i) | 6-C₃H₇(i) | H | —CH₂—CH₂—CH₂—CH₂—C₆H₅ | $n_{21}^D = 1.5581$ |
| 153 | 2-CH₃ | 6-CH₃ | 4-O-(3-F-C₆H₄) | —C₄H₉(t) | $n_{24}^D = 1.5640$ |
| 154 | 2-C₂H₅ | 6-C₄H₉(s) | 4-O-C₆H₅ | —CH(C₃H₇(i))(C₃H₇(i)) | |

-continued

| Compound | R$_1$ | R$_2$ | R$_3$ | R$_4$ | Physical data |
|---|---|---|---|---|---|
| 155 | 2-CH$_3$ | 6-CH$_3$ | 4-O–C$_6$H$_4$– | –CH(C$_2$H$_5$)$_2$ | |
| 156 | 2-CH$_3$ | 6-CH$_3$ | 4-O–(2,6-Cl$_2$-pyridin-3-yl) | –CH(C$_2$H$_5$)$_2$ | |
| 157 | 2-C$_3$H$_7$(i) | 6-C$_3$H$_7$(i) | 4-O–C$_6$H$_4$– | –CH(C$_2$H$_5$)$_2$ | |
| 158 | 2-C$_2$H$_5$ | 6-C$_4$H$_9$(s) | 4-O–C$_6$H$_4$– | –CH(C$_2$H$_5$)$_2$ | |
| 159 | 2-CH$_3$ | 6-CH$_3$ | 4-O–(4-F–C$_6$H$_4$)– | –CH(C$_2$H$_5$)$_2$ | |
| 160 | 2-C$_3$H$_7$(i) | 6-C$_3$H$_7$(i) | 4-O–C$_6$H$_4$– | –CH(C$_3$H$_7$)(CH$_3$) | |
| 161 | 2-C$_3$H$_7$(i) | 6-C$_3$H$_7$(i) | H | –CH(C$_2$H$_5$)$_2$ | |
| 162 | 2-CH$_3$ | 6-CH$_3$ | 4-O–C$_6$H$_4$– | –CH(C$_3$H$_7$(n))(CH$_3$) | |

-continued

| Compound | R₁ | R₂ | R₃ | R₄ | Physical data |
|---|---|---|---|---|---|
| 163 | 2-C₃H₇(i) | 6-C₃H₇(i) | 4-O-C₆H₄ | -CH(C₃H₇(n))(CH₃) | |
| 164 | 2-CH₃ | 6-CH₃ | 4-O-C₆H₄ | -CH(C₃H₇(i))(CH₃) | |
| 165 | 2-CH₃ | 6-CH₃ | 4-O-C₆H₄ | -(CH₂)₅CH₃ | |
| 166 | 2-CH₃ | 6-CH₃ | 4-O-C₆H₄ | -(CH₂)₁₁CH₃ | |
| 167 | 2-C₂H₅ | 6-C₂H₅ | H | -C₃H₇(i) | |
| 168 | 2-C₂H₅ | 6-C₂H₅ | 4-O-C₆H₄ | -C₃H₇(i) | |
| 169 | 2-C₂H₅ | 6-C₂H₅ | 4-O-C₆H₄ | -C₄H₉(t) | |
| 170 | 2-C₃H₇(i) | 6-C₃H₇(i) | 4-O-C₆H₄ | -C(CH₃)₂-C₂H₅ | |
| 171 | 2-C₂H₅ | 6-C₂H₅ | 4-O-C₆H₄ | cyclopentyl-H | |

-continued
| Compound | $R_1$ | $R_2$ | $R_3$ | $R_4$ | Physical data |
|---|---|---|---|---|---|
| 172 | 2-$C_2H_5$ | 6-$C_2H_5$ |  4-O— | —$C_4H_9(s)$ | |
| 173 | 2-$C_2H_5$ | 6-$C_2H_5$ | 4-O— | —$C(CH_3)_2$—$C_2H_5$ | |
| 174 | 2-$C_2H_5$ | 6-$C_2H_5$ | 4-O— | —$CH(CH_3)$—$CH_2$—O—$CH_3$ | |
| 175 | 2-$C_2H_5$ | 6-$C_4H_9(s)$ | 4-O— | —$C_4H_9(s)$ | |
| 176 | 2-$C_4H_9(s)$ | 6-$C_2H_5$ | 4-O— | —$CH(CH_3)$—$CH_2$—O—$CH_3$ | |
| 177 | 2-$C_2H_5$ | 6-$C_4H_9(s)$ | 4-O— | 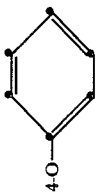 | |
| 178 | 2-$C_2H_5$ | 6-$C_4H_9(s)$ | 4-O— | —$C(CH_3)_2$—$C_2H_5$ | |
| 179 | 2-$C_2H_5$ | 6-$C_3H_7(i)$ | 4-O— | —$C_4H_9(s)$ | |

-continued

| Compound | R₁ | R₂ | R₃ | R₄ | Physical data |
|---|---|---|---|---|---|
| 180 | 2-C₂H₅ | 6-C₃H₇(i) | 4-O-C₆H₄ | —C(CH₃)₂—C₂H₅ | |
| 181 | 2-C₂H₅ | 6-C₃H₇(i) | 4-O-C₆H₄ | —CH(CH₃)—CH₂—O—CH₃ | |
| 182 | 2-C₂H₅ | 6-C₃H₇(i) | 4-O-C₆H₄ | cyclopentyl | |
| 183 | 2-C₃H₇(i) | 6-C₃H₇(i) | 4-O-C₆H₃F | —C₄H₉(t) | |
| 184 | 2-C₃H₇(i) | 6-C₃H₇(i) | 4-O-C₆H₃F | cyclopentyl | |

EXAMPLE 2

Formulations for liquid active ingredients of formula I according to Example 1 or combinations thereof with other insecticides or acaricides (throughout, percentages are by weight)

| 1. Emulsifiable concentrates | (a) | (b) | (c) |
|---|---|---|---|
| active ingredient or active ingredient combination | 25% | 40% | 50% |
| calcium dodecylbenzenesulfonate | 5% | 8% | 6% |
| castor oil polyethylene glycol ether (36 moles of ethylene oxide) | 5% | — | — |
| tributylphenol polyethylene glycol ether (30 moles of ethylene oxide) | — | 12% | 4% |
| cyclohexane | — | 15% | 20% |
| xylene mixture | 65% | 25% | 20% |

Emulsion of any required concentration can be produced from such concentrates by dilution with water.

| 2. Solutions | (a) | (b) | (c) | (d) |
|---|---|---|---|---|
| active ingredient or active ingredient combination | 80% | 10% | 5% | 95% |
| ethylene glycol monomethyl ether | 20% | — | — | — |
| polyethylene glycol 400 | — | 70% | — | — |
| N—methyl-2-pyrrolidone | — | 20% | — | — |
| expoxidised coconut oil | — | — | 1% | 5% |
| ligroin (boiling range 160–190°) | — | — | 94% | — |

These solutions are suitable for application in the form of microdrops.

| 3. Granulates | (a) | (b) |
|---|---|---|
| active ingredient or active ingredient combination | 5% | 10% |
| kaolin | 94% | — |
| highly dispersed silicic acid | 1% | — |
| attapulgite | — | 90% |

The active ingredient or active ingredient combination is dissolved in methylene chloride, the solution is sprayed onto the carrier, and the solvent is subsequently evaporated off in vacuo.

| 4. Dusts | (a) | (b) |
|---|---|---|
| active ingredient or active ingredient combination | 2% | 5% |
| highly dispersed silicic acid | 1% | 5% |
| talcum | 97% | — |
| kaolin | — | 90% |

Ready for use dusts are obtained by intimately mixing the carriers with the active ingredient or active ingredient combination.

Formulations for solid active ingredients of formula I according to Example 1 or combinations thereof with other insecticides or acaricides (throughout, percentages are by weight)

| 5. Wettable powders | (a) | (b) | (c) |
|---|---|---|---|
| active ingredient or active ingredient combination | 25% | 50% | 75% |
| sodium lignosulfonate | 5% | 5% | — |
| sodium laurylsulfate | 3% | — | 5% |
| sodium diisobutylnaphthalenesulfonate | — | 6% | 10% |
| octylphenol polyethylene glycol ether (7–8 moles of ethylene oxide) | — | 2% | — |
| highly dispersed silicic acid | 5% | 10% | 10% |
| kaolin | 62% | 27% | — |

The active ingredient or active ingredient combination is thoroughly mixed with the adjuvants and the mixture is thoroughly ground in a suitable mill, affording wettable powders which can be diluted with water to give suspensions of any desired concentration.

| 6. Emulsifiable concentrate | |
|---|---|
| active ingredient or active ingredient combination | 10% |
| octylphenol polyethylene glycol ether (4–5 moles of ethylene oxide) | 3% |
| calcium dodecylbenzenesulfonate | 3% |
| castor oil polyglycol ether (36 moles of ethylene oxide) | 4% |
| cyclohexanone | 30% |
| xylene mixture | 50% |

Emulsions of any required concentration can be obtained from this concentrate by dilution with water.

| 7. Dusts | (a) | (b) |
|---|---|---|
| active ingredient or active ingredient combination | 5% | 8% |
| talcum | 95% | — |
| kaolin | — | 92% |

Ready for use dusts are obtained by mixing the active ingredient or active ingredient combination with the carrier, and grinding the mixture in a suitable mill.

| 8. Extruder granulate | |
|---|---|
| active ingredient or active ingredient combination | 10% |
| sodium lignosulfonate | 2% |
| carboxymethylcellulose | 1% |
| kaolin | 87% |

The active ingredient or active ingredient combination is mixed and ground with the adjuvants, and the mixture is subsequently moistened with water. The mixture is extruded, granulated and then dried in a stream of air.

| 9. Coated granulate | |
|---|---|
| active ingredient or active ingredient combination | 3% |
| polyethylene glycol 200 | 3% |
| kaolin | 94% |

The finely ground active ingredient or active ingredient combination is uniformly applied, in a mixer, to the kaolin moistened with polyethylene glycol. Non-dusty coated granulates are obtained in this manner.

| 10. Suspension concentrate | |
|---|---|
| active ingredient or active ingredient combination | 40% |
| ethylene glycol | 10% |
| nonylphenol polyethylene glycol ether (15 moles of ethylene oxide) | 6% |
| sodium lignosulfonate | 10% |
| carboxymethylcellulose | 1% |
| 37% aqueous formaldehyde solution | 0.2% |
| silicone oil in the form of a 75% aqueous emulsion | 0.8% |

| 10. Suspension concentrate | |
|---|---|
| water | 32% |

The finely ground active ingredient or active ingredient combination is intimately mixed with the adjuvants, giving a suspension concentrate from which suspensions of any desired concentration can be obtained by dilution with water.

EXAMPLE 3

Action against *Musca domestica*

50 g of freshly prepared nutrient substrate for maggots are charged into each of a number of beakers. A specific amount of a 1% acetonic solutiion of the respective test compound is pipetted onto the nutrient substrate present in the beakers to give an active ingredient concentration of 400 ppm. The substrate is then thoroughly mixed and the acetone subsequently allowed to evaporate over a period of at least 20 hours.

Then 25 one-day-old maggots of *Musca domestica* are put into each of the beakers containing the treated nutrient substrate for testing with each active ingredient at the given concentration. After the maggots have pupated, the pupae are separated from the substrate by flushing them out with water and then deposited in containers closed with a perforated top.

Each batch of flushed out pupae is counted to determine the toxic effect of the test compound on the maggot development. A count is then made after 10 days of the number of flies which have hatched out of the pupae.

The compounds of formula I according to Example 1 have good activity in this test.

EXAMPLE 4

Action against *Lucilia sericata*

1 ml of an aqueous solution containing 0.5% of test compound is added to 9 ml of a culture medium. Then about 30 freshly hatched *Lucilia sericata* larvae are added to the culture medium, and the insecticidal action is determined after 48 and 96 hours by evaluating the mortality rate.

The compounds of formula I according to Example 1 exhibit good activity against in this test.

EXAMPLE 5

Action against *Aedes aegypti*

A concentration of 400 ppm is obtained by pipetting a specific amount of a 0.1% solution of the test compound in acetone onto the surface of 150 ml of water in a beaker. After the acetone has evaporated, 30 to 40 two-day-old larvae of *Aedes aegypti* are put into the beaker containing the test compound. Mortality counts are made after 2 and 7 days.

The compounds of formula I according to Example 1 exhibit good activity in this test.

EXAMPLE 6

Insecticidal action against feeding insects

Cotton plants (about 20 cm high) are sprayed with aqueous emulsions (obtained from a 10% emulsifiable concentrate) containing the respective test compound in concentrations of 100 to 400 ppm. After the spray coating has dried, the cotton plants are populated with *Spodoptera littoralis* and *Heliothis virescens* larvae in the L$_3$-stage. The test is carried out at 24° C. and 60% relative humidity. At 24 hour intervals, a mortality count is made and the larvae are also examined for inhibition of development and shedding.

80 to 100% mortality against Heliothis larvae is effected with compound 31 at 100 ppm and with compound 32 at 400 ppm.

At the following concentrations, the compounds of Example 1 effect 80 to 100% mortality against larvae of *Spodoptera littoralis:*

| Compound | Concentration |
|---|---|
| 32 | 200 ppm |
| 30, 79, 80, 81, 82, 84, 85 and 86 | 400 ppm |

EXAMPLE 7

Action against *Spodoptera littoralis* and *Heliothis virescens* (larvae and eggs)

Three cotton plants each having a height of about 15–20 cm and grown in pots are treated with a sprayable liquid preparation of the test compound in a concentration of 800 ppm. After the spray coating has dried, the potted plants are placed in a metal container having a capacity of about 20 liters and covered with a glass plate. The humidity in the interior of the covered container is regulated such that no water of condensation forms. Direct light falling on the plants is avoided. The three plants are then infested altogether with:

(a) 50 larvae of *Spodoptera littoralis* or *Heliothis virescens* in the L$_1$-stage;

(b) 20 larvae of *Spodoptera littoralis* or *Heliothis virescens* in the L$_3$-stage;

(c) 2 egg deposits of *Spodoptera littoralis* or *Heliothis virescens*. (The procedure is that two leaves of each plant are put into a plexiglass cylinder sealed at both ends with muslin. Two egg deposits of Spodoptera, or a part of a cotton leaf with eggs of Heliothis deposited thereon, are added to the leaves sealed in the cylinder.)

Evaluation in comparison with untreated controls is made after 4 and 5 days, taking into account the following criteria:

(a) the number of still living larvae, (b) inhibition of larval development and shedding, (c) feeding damage (shredding and perforation damage), (d) hatching rate (number of larvae hatched from the eggs).

In this test, the compounds of formula I according to Example 1 exhibit good overall activity.

EXAMPLE 8

Ovicidal action against *Spodoptera littoralis*

Eggs of *Spodoptera littoralis* deposited on filter paper are cut out of the paper and immersed in a solution of 400 ppm of test compound in a 1:1 mixture of acetone-water. The treated deposits are then removed from this mixture and kept in plastic dishes at 28° C. and 60% humidity. The hatching rate, i.e. the number of larvae which have developed from the treated eggs, is determined after 5 days.

Compounds 77, 78, 80, 81 and 88 according to Example 1 effect 80 to 100% mortality in this test.

EXAMPLE 9

Ovicidal action against *Laspeyresia pomonella* (eggs):

Egg deposits of *Laspeyrasia pomonella* not more than 24 hours old are immersed on filter paper for 1 minute in an aqueous acetonic solution containing 400 ppm of the test compound.

After the solution has dried, the eggs are placed in petri dishes and kept at a temperature of 28° C. The percentage of larvae hatched from the treated eggs is evaluated after 6 days.

In this test, compound 6 according to Example 1 effects 100% mortality even at 200 ppm.

EXAMPLE 10

Action against *Anthonomus grandis* (adults)

Two cotton plants in the 6-leaf stage, in pots, are each sprayed with a wettable aqueous emulsion formulation containing 400 ppm of the test compound. After the spray coating has dried (about 1½ hours), each plant is populated with 10 adult beetles (*Anthonomus grandis*). Plastic cylinders, covered at the top with gauze, are then slipped over the treated plants populated with the test insects to prevent the beetles from migrating from the plants. The treated plants are then kept at 25° C. and about 60% relative humidity. Evaluation is made after 2, 3, 4 and 5 days to determine the percentage mortality of the beetles (percentage in dorsal position) as well as the anti-feeding action as compared with untreated controls.

In this test, compounds 14, 77, 78 and 87 effect 80 to 100% mortality.

EXAMPLE 11

Action against plant-destructive acarids: *Tetranychus urticae* (OP-sensitive) and *Tetranychus cinnabarinus* (OP-tolerant)

16 hours before the test for acaricidal action, the primary leaves of *Phaseolus vulgaris* plants are infected with an infested piece of leaf from a mass culture of *Tetranychus urticae* (OP-sensitive) and *Tetranychus cinnabarinus* (OP-tolerant). (The tolerance refers to diazinone). The treated infested plants are sprayed to drip point with a test solution containing the respective test compound in concentrations of 0.75 to 400 ppm. A count of the number of living and dead imagines and larvae (all mobile stages) is made under a stereoscopic microscope after 24 hours and again after 7 days. One plant is used for each test compound at its given concentration and for each test species. During the test run, the plants are kept in greenhouse compartments at 25° C.

In this test, the compounds of formula I according to Example 1 show good activity against *Tetranychus urticae*.

At the following concentrations, the compounds of the invention effect 80 to 100% mortality against *Tetranychus cinnabarinus*:

| Compound | Concentration |
|---|---|
| 1 and 50 | 0.75 ppm |
| 26, 80, 82 and 83 | 12.5 ppm |
| 86 | 400 ppm |

EXAMPLE 12

Insecticidal contact against *Myzus persicae*

Pea plants which have been reared in water to a height of about 4 cm are each populated with about 200 individuals of the species *Myzus persicae* before the start of the test. The treated plants are then sprayed to drip point with an aqueous suspension containing the test compound in a concentration of 12.5, 50, 200 and 400 ppm. Two plants are used for each compound at its given concentration. A mortality count is made 48 hours after application. The test is carried out at 20°-22° C. and 60% relative humidity.

In this test, compound 8 effects 80 to 100% mortality even at a concentration of 12.5 ppm. 80 to 100% mortality is effected by compounds 32 and 33 at 50 ppm, by compounds, 30, 31 and 61 at 200 ppm and by compound 89 at 400 ppm.

EXAMPLE 13

Insecticidal contact action against *Aphis craccivora*

Before the start of the test, bean plants (*Vicia faba*) reared in pots are each populated with about 200 individuals of the species *Aphis craccivora*. The treated plants are sprayed 24 hours later to drip point with an aqueous formulation containing the test compound in a concentration of 12.5, 50, 100, 200 and 400 ppm. Two plants are used for each test compound at its given concentration and a mortality count is made after a further 24 hours.

In this test, the compounds of the invention effect 80 to 100% mortality at the concentrations listed in the following table:

| Compound | Concentration |
|---|---|
| 8, 43, 47 and 61 | 12.5 ppm |
| 30, 32, 33, 40, 42 and 44 | 50 ppm |
| 10, 12, 14, 82, 83, 87, 89 | 100 ppm |
| 31, 46, 52 and 53 | 200 ppm |
| 76, 77, 79, 84 and 85 | 400 ppm |

EXAMPLE 14

Action against *Laodelphax striatellus* and *Nilaparvata lugens* (nymphs)

The test is carried out with growing plants. The procedure is that 4 rice plants (thickness of stem 8 mm) about 20 cm in height are planted into each of a number of pots (diameter 8 cm). The plants in each pot are sprayed on a rotary table with 100 ml of acetonic solutions containing the test compound in concentrations of 50 ppm to 400 ppm. After the spray coating has dried, each plant is populated with 20 nymphs of the test organisms in the third stage. To prevent the cicadas from escaping, a glass cylinder which is open at both ends is slipped over each of the plants and sealed with a gauze top. The nymphs are kept for 10 days on the treated plant until the next development stage has been reached. Evaluation of percentage mortality is made 1, 4 and 8 days after treatment.

When used at the given concentrations, the following compounds of the invention effect 80 to 100% mortality after 8 days against nymphs of *Nilaparvata lugens*:

-continued

| 10. Suspension concentrate | |
|---|---|
| water | 32% |

The finely ground active ingredient or active ingredient combination is intimately mixed with the adjuvants, giving a suspension concentrate from which suspensions of any desired concentration can be obtained by dilution with water.

EXAMPLE 3

Action against *Musca domestica*

50 g of freshly prepared nutrient substrate for maggots are charged into each of a number of beakers. A specific amount of a 1% acetonic solutiion of the respective test compound is pipetted onto the nutrient substrate present in the beakers to give an active ingredient concentration of 400 ppm. The substrate is then thoroughly mixed and the acetone subsequently allowed to evaporate over a period of at least 20 hours.

Then 25 one-day-old maggots of *Musca domestica* are put into each of the beakers containing the treated nutrient substrate for testing with each active ingredient at the given concentration. After the maggots have pupated, the pupae are separated from the substrate by flushing them out with water and then deposited in containers closed with a perforated top.

Each batch of flushed out pupae is counted to determine the toxic effect of the test compound on the maggot development. A count is then made after 10 days of the number of flies which have hatched out of the pupae.

The compounds of formula I according to Example 1 have good activity in this test.

EXAMPLE 4

Action against *Lucilia sericata*

1 ml of an aqueous solution containing 0.5% of test compound is added to 9 ml of a culture medium. Then about 30 freshly hatched *Lucilia sericata* larvae are added to the culture medium, and the insecticidal action is determined after 48 and 96 hours by evaluating the mortality rate.

The compounds of formula I according to Example 1 exhibit good activity against in this test.

EXAMPLE 5

Action against *Aedes aegypti*

A concentration of 400 ppm is obtained by pipetting a specific amount of a 0.1% solution of the test compound in acetone onto the surface of 150 ml of water in a beaker. After the acetone has evaporated, 30 to 40 two-day-old larvae of *Aedes aegypti* are put into the beaker containing the test compound. Mortality counts are made after 2 and 7 days.

The compounds of formula I according to Example 1 exhibit good activity in this test.

EXAMPLE 6

Insecticidal action against feeding insects

Cotton plants (about 20 cm high) are sprayed with aqueous emulsions (obtained from a 10% emulsifiable concentrate) containing the respective test compound in concentrations of 100 to 400 ppm. After the spray coating has dried, the cotton plants are populated with *Spodoptera littoralis* and *Heliothis virescens* larvae in the $L_3$-stage. The test is carried out at 24° C. and 60% relative humidity. At 24 hour intervals, a mortality count is made and the larvae are also examined for inhibition of development and shedding.

80 to 100% mortality against Heliothis larvae is effected with compound 31 at 100 ppm and with compound 32 at 400 ppm.

At the following concentrations, the compounds of Example 1 effect 80 to 100% mortality against larvae of *Spodoptera littoralis:*

| Compound | Concentration |
|---|---|
| 32 | 200 ppm |
| 30,79, 80, 81, 82, 84, 85 and 86 | 400 ppm |

EXAMPLE 7

Action against *Spodoptera littoralis* and *Heliothis virescens* (larvae and eggs)

Three cotton plants each having a height of about 15-20 cm and grown in pots are treated with a sprayable liquid preparation of the test compound in a concentration of 800 ppm. After the spray coating has dried, the potted plants are placed in a metal container having a capacity of about 20 liters and covered with a glass plate. The humidity in the interior of the covered container is regulated such that no water of condensation forms. Direct light falling on the plants is avoided. The three plants are then infested altogether with:

(a) 50 larvae of *Spodoptera littoralis* or *Heliothis virescens* in the $L_1$-stage;

(b) 20 larvae of *Spodoptera littoralis* or *Heliothis virescens* in the $L_3$-stage;

(c) 2 egg deposits of *Spodoptera littoralis* or *Heliothis virescens*. (The procedure is that two leaves of each plant are put into a plexiglass cylinder sealed at both ends with muslin. Two egg deposits of Spodoptera, or a part of a cotton leaf with eggs of Heliothis deposited thereon, are added to the leaves sealed in the cylinder.)

Evaluation in comparison with untreated controls is made after 4 and 5 days, taking into account the following criteria:

(a) the number of still living larvae, (b) inhibition of larval development and shedding, (c) feeding damage (shredding and perforation damage), (d) hatching rate (number of larvae hatched from the eggs).

In this test, the compounds of formula I according to Example 1 exhibit good overall activity.

EXAMPLE 8

Ovicidal action against *Spodoptera littoralis*

Eggs of *Spodoptera littoralis* deposited on filter paper are cut out of the paper and immersed in a solution of 400 ppm of test compound in a 1:1 mixture of acetone-water. The treated deposits are then removed from this mixture and kept in plastic dishes at 28° C. and 60% humidity. The hatching rate, i.e. the number of larvae which have developed from the treated eggs, is determined after 5 days.

Compounds 77, 78, 80, 81 and 88 according to Example 1 effect 80 to 100% mortality in this test.

EXAMPLE 9

Ovicidal action against *Laspeyresia pomonella* (eggs):

Egg deposits of *Laspeyrasia pomonella* not more than 24 hours old are immersed on filter paper for 1 minute in an aqueous acetonic solution containing 400 ppm of the test compound.

After the solution has dried, the eggs are placed in petri dishes and kept at a temperature of 28° C. The percentage of larvae hatched from the treated eggs is evaluated after 6 days.

In this test, compound 6 according to Example 1 effects 100% mortality even at 200 ppm.

EXAMPLE 10

Action against *Anthonomus grandis* (adults)

Two cotton plants in the 6-leaf stage, in pots, are each sprayed with a wettable aqueous emulsion formulation containing 400 ppm of the test compound. After the spray coating has dried (about 1½ hours), each plant is populated with 10 adult beetles (*Anthonomus grandis*). Plastic cylinders, covered at the top with gauze, are then slipped over the treated plants populated with the test insects to prevent the beetles from migrating from the plants. The treated plants are then kept at 25° C. and about 60% relative humidity. Evaluation is made after 2, 3, 4 and 5 days to determine the percentage mortality of the beetles (percentage in dorsal position) as well as the anti-feeding action as compared with untreated controls.

In this test, compounds 14, 77, 78 and 87 effect 80 to 100% mortality.

EXAMPLE 11

Action against plant-destructive acarids: *Tetranychus urticae* (OP-sensitive) and *Tetranychus cinnabarinus* (OP-tolerant)

16 hours before the test for acaricidal action, the primary leaves of *Phaseolus vulgaris* plants are infected with an infested piece of leaf from a mass culture of *Tetranychus urticae* (OP-sensitive) and *Tetranychus cinnabarinus* (OP-tolerant). (The tolerance refers to diazinone). The treated infested plants are sprayed to drip point with a test solution containing the respective test compound in concentrations of 0.75 to 400 ppm. A count of the number of living and dead imagines and larvae (all mobile stages) is made under a stereoscopic microscope after 24 hours and again after 7 days. One plant is used for each test compound at its given concentration and for each test species. During the test run, the plants are kept in greenhouse compartments at 25° C.

In this test, the compounds of formula I according to Example 1 show good activity against *Tetranychus urticae*.

At the following concentrations, the compounds of the invention effect 80 to 100% mortality against *Tetranychus cinnabarinus*:

| Compound | Concentration |
| --- | --- |
| 1 and 50 | 0.75 ppm |
| 26, 80, 82 and 83 | 12.5 ppm |
| 86 | 400 ppm |

EXAMPLE 12

Insecticidal contact against *Myzus persicae*

Pea plants which have been reared in water to a height of about 4 cm are each populated with about 200 individuals of the species *Myzus persicae* before the start of the test. The treated plants are then sprayed to drip point with an aqueous suspension containing the test compound in a concentration of 12.5, 50, 200 and 400 ppm. Two plants are used for each compound at its given concentration. A mortality count is made 48 hours after application. The test is carried out at 20°–22° C. and 60% relative humidity.

In this test, compound 8 effects 80 to 100% mortality even at a concentration of 12.5 ppm. 80 to 100% mortality is effected by compounds 32 and 33 at 50 ppm, by compounds, 30, 31 and 61 at 200 ppm and by compound 89 at 400 ppm.

EXAMPLE 13

Insecticidal contact action against *Aphis craccivora*

Before the start of the test, bean plants (*Vicia faba*) reared in pots are each populated with about 200 individuals of the species *Aphis craccivora*. The treated plants are sprayed 24 hours later to drip point with an aqueous formulation containing the test compound in a concentration of 12.5, 50, 100, 200 and 400 ppm. Two plants are used for each test compound at its given concentration and a mortality count is made after a further 24 hours.

In this test, the compounds of the invention effect 80 to 100% mortality at the concentrations listed in the following table:

| Compound | Concentration |
| --- | --- |
| 8, 43, 47 and 61 | 12.5 ppm |
| 30, 32, 33, 40, 42 and 44 | 50 ppm |
| 10, 12, 14, 82, 83, 87, 89 | 100 ppm |
| 31, 46, 52 and 53 | 200 ppm |
| 76, 77, 79, 84 and 85 | 400 ppm |

EXAMPLE 14

Action against *Laodelphax striatellus* and *Nilaparvata lugens* (nymphs)

The test is carried out with growing plants. The procedure is that 4 rice plants (thickness of stem 8 mm) about 20 cm in height are planted into each of a number of pots (diameter 8 cm). The plants in each pot are sprayed on a rotary table with 100 ml of acetonic solutions containing the test compound in concentrations of 50 ppm to 400 ppm. After the spray coating has dried, each plant is populated with 20 nymphs of the test organisms in the third stage. To prevent the cicadas from escaping, a glass cylinder which is open at both ends is slipped over each of the plants and sealed with a gauze top. The nymphs are kept for 10 days on the treated plant until the next development stage has been reached. Evaluation of percentage mortality is made 1, 4 and 8 days after treatment.

When used at the given concentrations, the following compounds of the invention effect 80 to 100% mortality after 8 days against nymphs of *Nilaparvata lugens:*

| Compound | Concentration |
| --- | --- |
| 43 | 12.5 ppm |
| 12, 14, 40 and 41 | 50 ppm |
| 8, 19, 82 and 87 | 100 ppm |
| 30, 33 and 53 | 200 ppm |
| 31, 32, 44, 54, 55, 65, 80, 81, 83, 84, 85 and 89 | 400 ppm |

Good activity against nymphs of *Laodelpax striatellus* can also be achieved with the compounds of formula I according to Example 1.

EXAMPLE 15

Action against soil insects (*Diabrotica balteata*)

350 ml of soil (consisting of 95 vol.% of sand and 5 vol.% of peat) are mixed with 150 ml of each of a number of aqueous emulsion formulations which contain the test compound in increasing concentrations of 3 ppm to 200 ppm. Plastic beakers with a diameter of about 10 cm at the top are then partly filled with the treated soil. Ten $L_3$ larvae of *Diabrotica balteata* are put into each beaker, then 4 maize seedlings are planted and the beaker is filled up with soil. The beakers are sealed with plastic sheeting and kept at about 22° C. Ten days later the soil in the beakers is sieved and a mortality count of the remaining larvae is made.

In this test, the following compounds of the invention effect 80 to 100% mortality at the concentrations listed in the following table:

| Compound | Concentration |
| --- | --- |
| 30 and 43 | 3 ppm |
| 32, 42, 44 and 53 | 12.5 ppm |
| 33, 36, 41, 52 and 61 | 50 ppm |
| 66, 78, 87, 88 and 106 | 100 ppm |
| 14 | 200 ppm |
| 77, 80, 84 and 89 | 400 ppm |

EXAMPLE 16

Action against *Panonychus ulmi* (OP and carbamate resistant)

Potted apple seedlings with about 20 to 30 leaves are each populated with 60 adult females of *Panonychus ulmi*. The infested plants are sprayed 7 days after to drip point with an aqueous emulsion containing 0.75 ppm of the test compound. The treated plants are then stood in a greenhouse for a further 14 days at 25° C. and about 50% relative humidity.

After this period, evaluation is made by taking 20 leaves from each plant, removing the mite population from these leaves by means of a brushing device and counting the number of eggs, postembryonic stages and adults under a stereoscopic microscope. An assessment is made of the percentage reduction of the mite population as compared with untreated controls.

In this test, compounds 1 and 26 according to Example 1 effect 80 to 100% mortality.

What is claimed is:

1. A compound of formula I

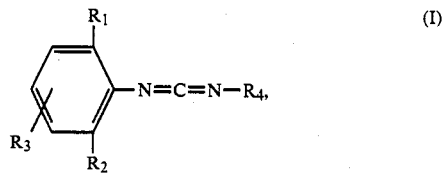

wherein
$R_1$ is hydrogen, fluorine, chlorine, $C_1$-$C_4$alkyl, methoxy, ethoxy, trifluoromethoxy or $C_1$-$C_3$alkylthio;
$R_2$ is hydrogen, fluorine, chlorine, $C_1$-$C_4$alkyl, methoxy or ethoxy;
$R_3$ is pyrid-2-yloxy or pyrid-2-yloxy which is mono- or disubstituted by a member selected from the group consisting of halogen and $C_1$-$C_3$haloalkyl having 1 to 7 halogen atoms;
$R_4$ is $C_1$-$C_{12}$alkyl, alkoxyalkyl having a total of 2 to 10 carbon atoms, $C_3$-$C_{10}$cycloalkyl, $C_3$-$C_{10}$cycloalkylmethyl, $C_3$-$C_{10}$cycloalkyl which is substituted by 1 to 3 $C_1$-$C_3$alkyl groups, or is $C_1$-$C_5$alkyl which is substituted by 1 or 2 $C_3$-$C_{10}$cycloalkyl groups, or is a polycyclic alkyl group having 7 to 10 carbon atoms, phenyl($C_1$-$C_5$)alkyl or phenyl($C_1$-$C_5$)alkyl which is mono- or disubstituted at the phenyl nucleus by halogen, trifuloromethyl, methoxy or ethoxy.

2. A compound according to claim 1, wherein $R_4$ is isopropyl or tert-butyl.

3. A compound according to claim 1, wherein
$R_3$ is pyrid-2-yloxy or pyrid-2-yloxy which is mono- or disubstituted by a member selected from the group consisting of halogen and trifluoromethyl; and
$R_4$ is $C_1$-$C_{10}$alkyl, alkoxyalkyl having a total of 2 to 10 carbon atoms, $C_3$-$C_{10}$cycloalkyl, $C_3$-$C_{10}$cycloalkylmethyl, or $C_3$-$C_{10}$cycloalkyl which is substituted by a $C_1$-$C_3$alkyl group.

4. A compound according to claim 1, wherein
$R_3$ is pyrid-2-yloxy or pyrid-2-yloxy which is mono- or disubstituted by a member selected from the group consisting of fluorine, chlorine and trifluoromethyl; and
$R_4$ is $C_3$-$C_8$alkyl, alkoxyalkyl having a total of 2 to 7 carbon atoms, $C_3$-$C_8$cycloalkyl, $C_3$-$C_6$cycloalkylmethyl, methyl($C_3$-$C_6$)cycloalkyl, phenyl($C_1$-$C_4$)alkyl or phenyl ($C_1$-$C_4$)alkyl which is mono- or disubstituted at the phenyl nucleus by chlorine, trifluoromethyl or methoxy.

5. A compound according to claim 4, wherein
$R_1$ is hydrogen, fluorine, chlorine, $C_2$-$C_4$alkyl or methoxy;
$R_2$ is hydrogen, chlorine, $C_3$-$C_4$alkyl or methoxy;
$R_3$ is pyrid-2-yloxy or pyrid-2-yloxy which is mono- or disubstituted by chlorine and/or trifluoromethyl; and
$R_4$ is $C_3$-$C_8$alkyl, $C_1$-$C_4$alkoxy($C_1$-$C_3$)alkyl, $C_3$-$C_6$cycloalkyl, phenyl($C_1$-$C_4$)alkyl or phenyl($C_1$-$C_4$)alkyl which is substituted at the phenyl nucleus by a chlorine atom or a methoxy group.

6. A compound according to claim 1, wherein radical $R_3$ is in the 4-position.

7. A compound according to claim 1, wherein $R_1$ and $R_2$ are independent of each other and are methyl or ethyl.

8. A compound according to claim 6 of the formula

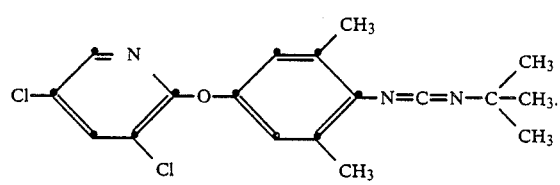

9. The compound of the formula

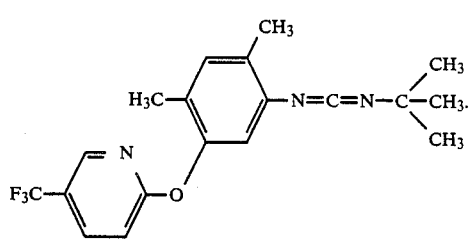

10. The compound according to claim 6 of the formula

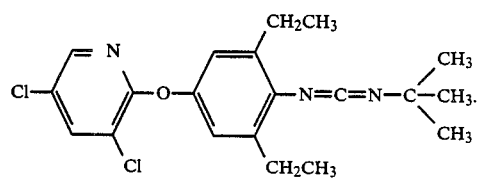

11. The compound according to claim 6 of the formula

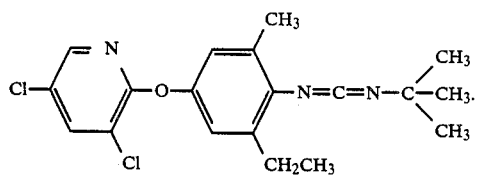

12. The compound according to claim 6 of the formula

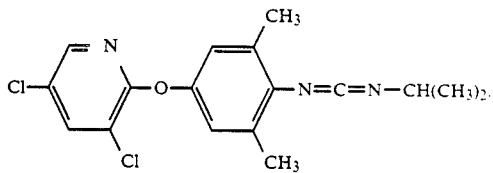

13. The compound according to claim 6 of the formula

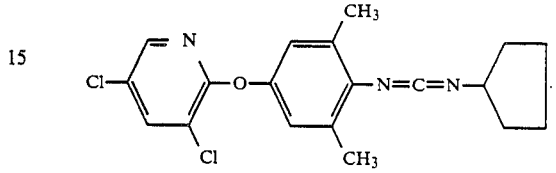

14. The compound according to claim 6 of the formula

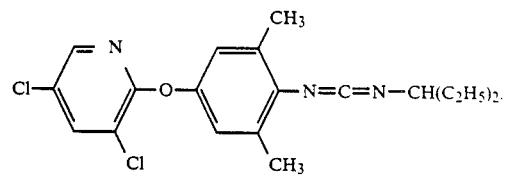

15. A pesticidal composition which comprises as active ingredient an effective amount of a compound according to claim 1, in combination with a suitable carrier or adjuvant.

16. A method of controlling pests selected from insects and representatives of the order Acarina, which method comprises contacting or treating said pests, their various development stages or the locus thereof with a pesticidally effective amount of a compound of formula I according to claim 1.

17. A method according to claim 16 for controlling insects or representatives of the order Acarina on animals and plants.

18. A method according to claim 17 for controlling plant-destructive insects.

19. A method of controlling ectoparasites selected from *Lucilia sericata* and ticks in domestic animals and productive livestock, which method comprises treating said animals or their habitat with an ectoparasitically effective amount of a compound of formula I according to claim 1.

* * * * *